US006736809B2

(12) United States Patent
Capuano et al.

(10) Patent No.: US 6,736,809 B2
(45) Date of Patent: May 18, 2004

(54) METHOD AND DEVICE FOR TREATMENT OF ANEURYSMS

(75) Inventors: Leonilda Capuano, Montreal (CA); Daniel Nahon, Ottawa (CA); Michael Urick, Beaconsfield (CA); Willard W. Hennemann, Hudson (CA); Patrick Chauvet, St-Laurent (CA)

(73) Assignee: CryoCath Technologies Inc., Kirkland (CA)

( * ) Notice: Subject to any disclaimer, the term of this patent is extended or adjusted under 35 U.S.C. 154(b) by 0 days.

(21) Appl. No.: 09/964,264

(22) Filed: Sep. 26, 2001

(65) Prior Publication Data

US 2003/0060814 A1 Mar. 27, 2003

(51) Int. Cl.[7] .................................... A61B 18/18
(52) U.S. Cl. .................................... 606/21; 606/23
(58) Field of Search .................................... 607/104, 105, 607/106; 606/20–25, 194, 96.01

(56) References Cited

U.S. PATENT DOCUMENTS

| | | | | |
|---|---|---|---|---|
| 5,281,215 A | | 1/1994 | Milder | |
| 5,370,608 A | | 12/1994 | Sahota et al. | |
| 5,417,653 A | | 5/1995 | Sahota et al. | |
| 5,423,807 A | | 6/1995 | Milder | |
| 5,704,913 A | | 1/1998 | Abele et al. | |
| 5,868,735 A | | 2/1999 | Lafontaine | |
| 5,902,299 A | | 5/1999 | Jayaraman | |
| 5,971,979 A | | 10/1999 | Joye et al. | |
| 6,012,457 A | | 1/2000 | Lesh | |
| 6,024,740 A | | 2/2000 | Lesh et al. | |
| 6,036,697 A | | 3/2000 | DiCaprio | |
| 6,051,019 A | | 4/2000 | Dobak, III | |
| 6,126,684 A | * | 10/2000 | Gobin et al. | 607/106 |
| 6,241,718 B1 | | 6/2001 | Arless et al. | |
| 6,386,202 B1 | * | 5/2002 | Frazee | 128/898 |
| 6,428,563 B1 | * | 8/2002 | Keller | 607/105 |
| 6,468,297 B1 | * | 10/2002 | Williams et al. | 607/113 |

* cited by examiner

*Primary Examiner*—Roy D. Gibson
(74) *Attorney, Agent, or Firm*—Christopher & Weisberg, P.A.

(57) ABSTRACT

A method is disclosed for treating an aneurysm by cooling a target tissue region of the aneurysm to a temperature below temperature for a preselected time period. The method entails thickening, strengthening, or increasing the density of a blood vessel wall by cooling the blood vessel wall with a cryogenically cooled device. In particular, a device having a heat conductive cooling chamber is disposed proximate to the aneurysm site; and a cryogenic fluid coolant is directed to flow inside the chamber to create endothermic cooling relative to the aneurysm. The method also promotes the growth of collagen and elastin in vascular tissue. Tissue cooling temperatures range from +20 to −20 degrees Celsius. The duration of treatment by application of cooling ranges from 15 seconds to up to 20 minutes or more. The method includes treating the aneurysm both from inside and outside the blood vessel wall forming the aneurysm.

7 Claims, 1 Drawing Sheet

11
15
13
12
F
F
10
14

METHOD AND DEVICE FOR TREATMENT OF ANEURYSMS

CROSS-REFERENCE TO RELATED APPLICATION

None

STATEMENT REGARDING FEDERALLY SPONSORED RESEARCH OR DEVELOPMENT n/a

FIELD OF THE INVENTION

The present invention relates to a method and device for treating aneurysms, and in particular, to a method involving the use of cryogenically cooled devices to cold treat tissue.

BACKGROUND OF THE INVENTION

Aneurysms are distensions formed by the localized dilation of the wall of an artery, a vein, or the heart. An aneurysm balloons due to the pressure of blood flowing through an area weakened due to disease, injury, or congenital defect. A "true" or common aneurysm results from the formation of a sac by the arterial wall, or tunica media, which remains unbroken, and may be associated with atherosclerosis. In a "false" or dissecting aneurysm, usually caused by trauma, a fissure in the wall of a blood vessel allows blood to escape into surrounding tissues and form a clot.

Doctors typically monitor the inflammation and progression of aneurysms using devices known in the art such as MRI and CT scanners and by observation of known patient symptoms. Typically, however, early stage aneurysms do not warrant dangerous surgical procedures, even if minimally invasive, due to the associated morbidity risk. Accordingly, the doctors choose a "wait and see" approach. Because surgery for aneurysms is risky, the surgeon may wait for the aneurysm to expand to a certain size before operating, when the risk of complications exceeds the risk of surgery. Accordingly, it would be desirable to treat aneurysms upon early detection rather than wait until they progress to a stage that requires dangerous, expensive surgery, or become life-threatening conditions.

Therefore, it would be desirable to have a device, coupled with a minimally invasive method, to retard, arrest and even reverse, the processes that lead to aneurysm formation.

SUMMARY OF THE INVENTION

A method is disclosed for treating an aneurysm, including the steps of cooling a target tissue region of the aneurysm to a predetermined temperature for a preselected time period. A method is also disclosed for thickening, strengthening, or increasing the density of a blood vessel wall, including the steps of cooling the blood vessel wall to a temperature below body temperature. In particular, a method is disclosed for treating an aneurysm, including the steps of: (i) providing a device having a heat conductive cooling chamber; (ii) disposing the cooling chamber proximate to the aneurysm; and (iii) directing the flow of cryogenic fluid inside the chamber to create endothermic cooling relative to the aneurysm. Finally, a method is disclosed for promoting growth of collagen and elastin in vascular tissue, including the steps of cooling the tissue for a predetermined period of time to a temperature below body temperature for a preselected time period.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Catheter based devices enable access to the weakened arterial wall around an aneurysm, are minimally invasive, and may be employed for a variety of diagnostic and therapeutic functions. Localized application of cold temperatures to the blood vessel wall may serve to strengthen and thicken the distended and dilated tissue of an aneurysm, as well as to make such tissue layers more dense. Accordingly, by applying such cold, or cryotreatment, to the aneurysm site, the aneurysm may be effectively treated without major surgery.

Figure 1:
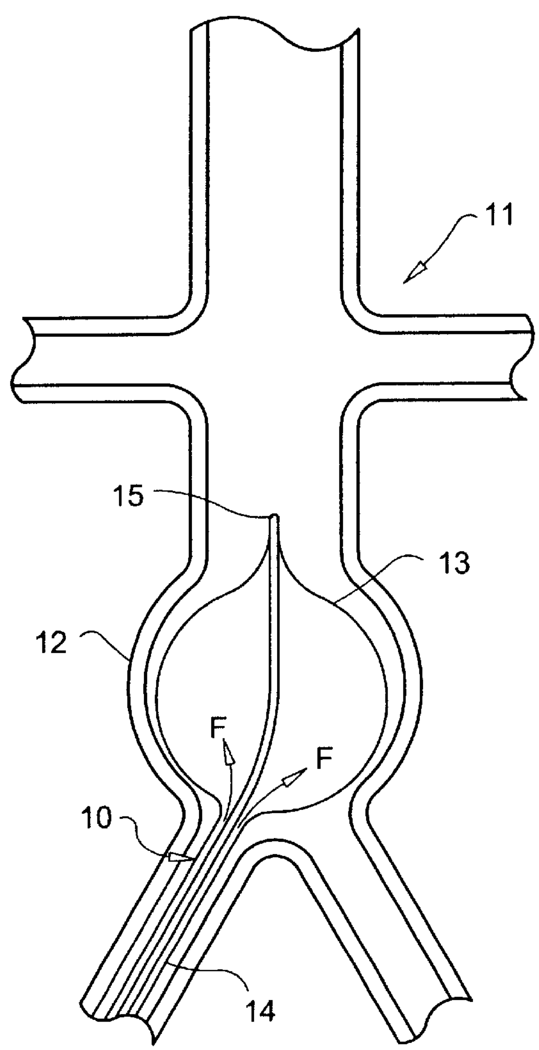
FIG. 1 is a cross-sectional view of a balloon catheter device disposed inside of a blood vessel proximate an aneurysm.

FIG. 1 illustrates a blood vessel and a device during a procedure for cryotreatment of an aneurysm. In FIG. 1, a balloon catheter, labeled generally as 10, is disposed inside of a blood vessel 11 proximate to an aneurysm 12. The balloon catheter 10 includes a flexible, expandable membrane or balloon 13 coupled to a catheter tube 14, wherein the catheter 10 is guided to the desired treatment site via a guidewire 15. In this procedure, the balloon catheter 10 is percutaneously inserted into the vasculature and advanced to the locus of the aneurysm 12. The specific size and shape of the balloon 13 and catheter tube 14 may be determined a priori in order to best fit the targeted artery or blood vessel where an aneurysm has formed. The balloon 13 is thereby inflated to appose the inner walls of the blood vessel proximate the aneurysm 12, so as to enable cryotreatment of the aneurysm 12 tissue.

However, contrary to conventional angioplasty procedures, the dilatation and apposition of the balloon 13 versus the inner walls of the aneurysm is not meant to dilate the blood vessel walls. Rather, the device employed in this procedure uses a balloon-tipped catheter configured to receive the flow of a coolant, or cryogenic fluid, therein. High pressure coolant fluid is connected to the proximal section of the catheter tube 14, which contains several tubes and lumens (not shown) adapted to contain the flow of coolant therein. The coolant used may be any stable working fluid capable of being compressed to high pressure, pumped though small diameter devices, and expanded to produce endothermic cooling at a desired location. Examples of such coolants are nitrogen, nitrous oxide, or any conventionally used refrigerant. The coolant may be in liquid, gaseous, or mixed phase form. The flow system inside of the catheter may be either closed loop, wherein the injected coolant is returned to the source for recycling and re-entry into the device, or open loop, wherein the coolant is pumped through the device only once, whereupon it exits outside the body and is discarded.

The coolant flows through the catheter tube 14 and is injected, generally along coolant flow lines F, into the balloon 13 at the distal tip of the catheter 10, whereupon the balloon 13 expands as the coolant is both vaporized and expanded inside the balloon. The combined evaporation and expansion of the coolant creates endothermic cooling in the near field of the balloon 13. The process is endothermic in that heat, or thermal energy, is absorbed by the balloon 13, and flow of coolant therein, from the surrounding environment: the aneurysm and targeted tissue of the blood vessel wall which forms the aneurysm. This cooling draws heat from the adjacent aneurysm tissue in the coolant flow inside of balloon 13, thereby cooling the aneurysm tissue to temperatures in the range of +20 to −20 degrees Centigrade.

The particular shape of the expanded balloon 13 may be predetermined by the use of a preformed balloon membrane, a memory retaining material, or other structural attribute wherein the expanded balloon 13 is configured to form a particular shape, yet also remain somewhat conformable. The balloon 13 may also be totally conformable, such that the expanded membrane fits to conform to the particular contours of the blood vessel wall of the aneurysm 12, for optimal contact therewith.

Alternatively, the distal tip of the catheter 10 may also include multiple expandable membranes or chambers (not shown), wherein different injection fluids are pumped into separate chambers within a single membrane, or multiple outer membranes. One injection fluid may be used to expand a first chamber, while another cooling fluid may be used to create endothermic cooling in the same or another chamber, as discussed above.

Any tissue near or adjacent to the balloon and flow of coolant therein may be cooled to temperatures below body temperature. The duration of cooling may vary from 15 seconds to up to 20 minutes, depending on the application, and the particular aneurysm targeted. Part or all of the surface of the balloon may be specially treated or affixed with heat conductive elements to create a pattern of cooling on the tissue surfaces targeted. An example of such an endovascular balloon catheter used to cold treat tissues is disclosed in U.S. Pat. No. 6,283,959 B1, the entirety of which is incorporated herein by reference. The tissue forming the aneurysm 12 is thus cold-treated by the catheter device 10, whereupon the balloon 13 is contracted or evacuated, and withdrawn from the treatment site.

The cryotreatment of aneurysm tissue in the prescribed time and temperature ranges discussed above may, among other effects, stimulate a tissue response which results in myointimal thickening of the blood vessel wall and anvential tissue. This thickening helps to minimize the incidence of aneurysm rupture, which can be fatal. Cryotreatment may also result in reparative regeneration of the endothelium, in addition to accelerated myointimal thickening. These overall effects serve to treat and possibly reverse the formation of an aneurysm, leading to significant therapeutic results.

Aneurysmal enlargement results in part from degradation of the extracellular matrix and other structural elements of the blood vessel wall. This in turn is related to an increased activity of proteolytic enzymes such as collagenase and elastase, resulting in destruction of collagen and elastin forming the blood vessel wall. Macrophages and inflammatory cells may also be sources of enzymes which have a capacity to degrade all the major connective tissues forming the blood vessel wall, including collagen and elastin, all of which contribute to aneurysms. The application of cold temperatures to such tissues may slow or retard the action of such macrophages, proteolytic enzymes, thus diminishing the destruction of collagen and elastin that is vital to the structural integrity of the blood vessel wall. In such a way, cryotreatment may effectively treat aneurysms.

Furthermore, for large blood vessels such as the aorta, aneurysms also exhibit the synthesis and accumulation of new collagen and elastin in the expanding aorta. However, these newly synthesized proteins often lack the intricate fibrillar structure and mature cross-linking necessary to maintain the normal tensile strength of the cellular matrix of the aortic wall. Cryotreatment of such areas may show the ability to compensate for such an effect, allowing the enlarged aortic wall to retain its normal extra-cellular matrix characteristics.

In general, the balloon 13 as used for cryotreatment, is an apposition device, and not a dilatation device. Accordingly, the strength of materials forming the balloon 13 itself, as well as the fluid pressures therein, are generally not required to be as high as a conventional blood vessel-dilating angioplasty balloon.

The catheter 10 itself may also be combined with an injection element, wherein a therapeutic drug or medication is infused in the target area around the aneurysm 12 in conjunction with the use of the balloon 13 to effect cryotreatment.

Figure 2:
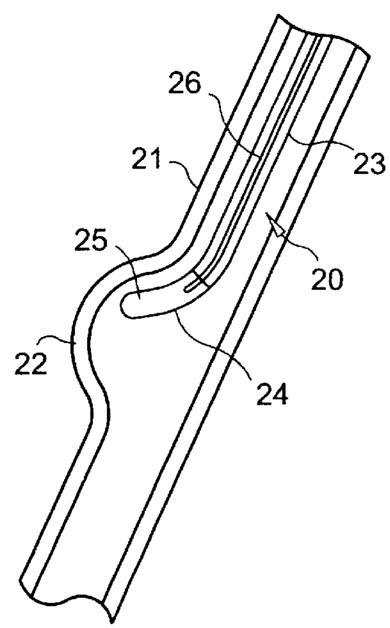
FIG. 2 is a cross-sectional view of a catheter with a cooling segment positioned proximate the arterial wall in an aneurysm.

In another procedure, a fixed diameter catheter device is used, as illustrated in FIG. 2. FIG. 2 shows an endovascular catheter 20 disposed inside of a blood vessel 21 near an aneurysm 22. The catheter 20 includes a catheter tube 23 having a cooling segment 24 disposed at its distal end portion. The catheter 20 may include one or more injection lumens 26, as well as several tubes and lumens (not shown) adapted to contain the flow of coolant therein. Although the distal end of the catheter 20 is shown in a substantially linear or straight configuration, the distal tip can be configured or commanded to assume an annular or helical shape. The catheter 20 is percutaneously inserted into the vasculature and advanced to the aneurysm site 22. A guidewire, rapid-exchange system, or other catheter positioning device may be employed to position the catheter tip at the desired location. Cooolant is injected into the catheter 20 via injection lumen 26, and flows through to the distal tip of the catheter, which contains the cooling segment 24. The cooling segment 24 is any heat conductive element which defines a closed volume expansion chamber 25, wherein coolant may be expanded to low temperatures after it exits the injection lumen 26. The coolant, which may be in mixed liquid or gaseous phase, is injected into the expansion chamber 25, whereby it undergoes both evaporative cooling through a change in phase from liquid to gas, and expansive cooling through a Joule-Thomson throttling process, similar to the those thermodynamic changes discussed with respect to the balloon catheter device 10 of FIG. 1. As with the balloon catheter device 10 embodiment above, these gas-dynamic processes are generally endothermic with respect to the surrounding environment, in that heat is drawn from the tissue forming the surrounding aneurysm 22 so as to cool such tissue to temperatures below normal human body temperature, and indeed below the freezing point of water and beyond. The strength of cooling may be controllably varied by the user by controlling the pressure and flow of coolant in the catheter device. The size and particular shape of the cooling segment 24 may be varied to best fit the contours of the particular aneurysm to be treated, such as a berry aneurysm in the brain, a saccular aortic aneurysm just above the heart, or a fusiform aneurysm in the lower aorta, as is illustrated in FIG. 1.

Figure 3:
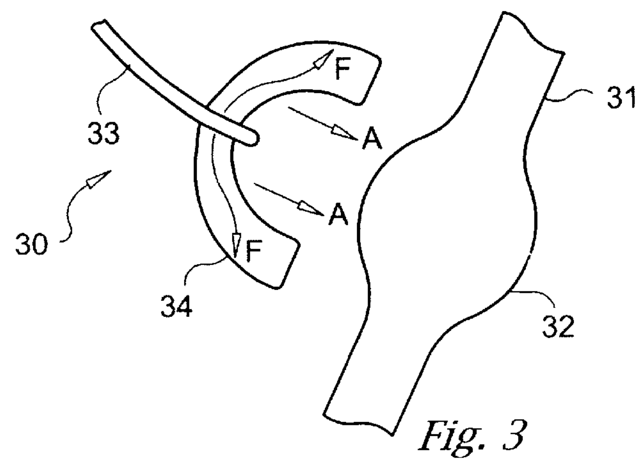
FIG. 3 is a perspective view of a balloon-cuff catheter device for contact with an aneurysm outside the arterial wall.

Although FIGS. 1 and 2 illustrate an approach to treating an aneurysm from within a blood vessel, FIG. 3 shows another embodiment wherein an aneurysm can be approached from the exterior of a blood vessel. In these procedures, the device can be a fixed diameter catheter, a probe, an inflatable device, which is applied to the surface of the aneurysm, or even a fixed, compliant, or inflatable cuff which partially or completely encircles the vessel in the location of the aneurysm, as shown in FIG. 3.

FIG. 3 illustrates a cryotreatment device 30, externally disposed adjacent to or proximate a blood vessel 31 having an aneurysm 32. The device 30 includes a coolant source element 33 having an expandable, inflatable membrane, such as the cuff 34 shown in FIG. 3. The cuff 34 may have a U-shape in order to conformably fit around one hemisphere of a rounded aneurysm 32, as shown in FIG. 3. Alternatively, the cuff 34 may be highly compliant and conformable such that when apposed against an aneurysm of any shape, the outer surface of such cuff 34 conformably rests in contact with such surface and envelops a significant surface area of the aneurysm.

The device 30 includes at least one injection lumen (not shown) in the source element 33 to carry the flow of coolant into the interior of cuff 34. The coolant may then be injected into the cuff 34, such as along the flow lines F shown in FIG. 3. As with the balloon catheter device 10 shown in FIG. 1, the cuff 34 is inflatably expandable by the action of a gas or liquid which may include the coolant or a completely separate source. The cuff 34 may be a preformed balloon membrane, or may include a memory retaining material or other structural attribute wherein the expanded form is configured to form a particular shape, yet also remain somewhat conformable.

Once inflated, the cuff 34 is externally applied in proximity to, or in apposition against, the desired aneurysm treatment site, such as in the direction of arrows A shown in FIG. 3. The flow of coolant in the cuff 34 endothermically cools the target tissue of the aneurysm 32, in accordance with the previous two embodiments of the present invention. This approach may be combined with conventional surgery to treat the aneurysm, wherein the cold treatment of the arterial wall is used with other treatment techniques and therapies.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for treating an aneurysm, comprising:

cooling only a target tissue region of the aneurysm to a temperature below +20 degrees Celsius for a time period between 15 seconds and twenty minutes, to inhibit aneurysm progression, portions of the target tissue region being selectively cooled to result in a pattern of cooling on surfaces of the target tissue region.

2. A method of thickening, strengthening, or increasing the density of a blood vessel wall, comprising:

cooling the blood vessel wall to a temperature below +20 degrees Celsius for a time period between 15 seconds and twenty minutes, to thicken, strengthen or increase the density of the blood vessel wall, portions of the target tissue region being selectively cooled to result in a pattern of cooling on surfaces of the target tissue region.

3. The method of claim 2, wherein the temperature is less than −20 degrees Celsius.

4. The method of claim 2, wherein the cooling is applied from the interior of the blood vessel.

5. A method of thickening, strengthening, or increasing the density of a blood vessel wall, comprising:

cooling the blood vessel wall to a temperature below +20 degrees Celsius for a time period between 15 seconds and twenty minutes, wherein the cooling is applied from the exterior of the blood vessel.

6. A method for treating an aneurysm, comprising the steps of:

a) providing a device having a cooling surface conformable to a tissue surface, the device having a heat conductive cooling member comprising a chamber and an expandable cooling structure including an inflatable element;

b) disposing the cooling member proximate to the aneurysm;

c) activating the cooling member to directly cool a portion of tissue comprising the aneurysm, to inhibit aneurysm progression, the cooling member to cool the tissue to a temperature below +20 degrees Celsius for a time period between 15 seconds and twenty minutes, wherein the step of activating the cooling member comprises directing the flow of cryogenic fluid into the chamber; and d) applying a therapeutic drug to the aneurysm.

7. A method for treating an aneurysm, comprising the steps of:

a) providing a device having a heat conductive cooling member;

b) disposing the cooling member proximate to the aneurysm; and c) activating the cooling member to directly cool a portion of tissue comprising the aneurysm, wherein the cooling member comprises a fixed diameter cooling surface, the cooling member to cool the tissue to a temperature below +20 degrees Celsius for a time period between 15 seconds and twenty minutes.

* * * * *